(12) United States Patent  (10) Patent No.: US 7,828,824 B2
Kwak et al.  (45) Date of Patent: Nov. 9, 2010

(54) FACET JOINT PROSTHESIS

(75) Inventors: SeungKyu Daniel Kwak, Grafton, MA (US); Amie Borgstrom, Stanford, CA (US); Erasmo Lopez, Seattle, WA (US); John Riley Hawkins, Cumberland, RI (US); Douglas R. LaSota, Saugus, MA (US); Charles M. Bartish, Jr., Providence, RI (US)

(73) Assignee: DePuy Spine, Inc., Raynham, MA (US)

( * ) Notice: Subject to any disclaimer, the term of this patent is extended or adjusted under 35 U.S.C. 154(b) by 737 days.

(21) Appl. No.: 11/611,420

(22) Filed: Dec. 15, 2006

(65) Prior Publication Data

US 2008/0147195 A1    Jun. 19, 2008

(51) Int. Cl.
*A61B 17/70* (2006.01)
(52) U.S. Cl. .................. 606/257; 606/259; 606/267
(58) Field of Classification Search ......... 606/246–278, 606/300–321; 623/17.11–17.16
See application file for complete search history.

(56) References Cited

U.S. PATENT DOCUMENTS

| | | | |
|---|---|---|---|
| 5,571,191 A | 11/1996 | Fitz | |
| 5,643,259 A * | 7/1997 | Sasso et al. | 606/264 |
| 6,001,130 A | 12/1999 | Bryan et al. | |
| 6,132,464 A | 10/2000 | Martin | |
| 6,419,703 B1 | 7/2002 | Fallin | |
| 6,783,528 B2 | 8/2004 | Vincent-Prestigiacomo et al. | |
| 7,083,621 B2 | 8/2006 | Shaolian et al. | |
| 7,125,410 B2 | 10/2006 | Freudiger et al. | |
| 2002/0065557 A1 | 5/2002 | Goble et al. | |
| 2002/0072800 A1 | 6/2002 | Goble et al. | |
| 2002/0123806 A1 | 9/2002 | Reiley | |
| 2003/0028250 A1 | 2/2003 | Reiley et al. | |
| 2003/0171750 A1 | 9/2003 | Chin | |
| 2004/0254574 A1 * | 12/2004 | Morrison et al. | 606/61 |
| 2005/0033431 A1 | 2/2005 | Gordon et al. | |
| 2005/0033432 A1 | 2/2005 | Gordon et al. | |
| 2005/0261685 A1 * | 11/2005 | Fortin et al. | 606/61 |
| 2006/0149228 A1 | 7/2006 | Schlapfer et al. | |
| 2006/0189985 A1 | 8/2006 | Lewis | |
| 2006/0200130 A1 | 9/2006 | Hawkins et al. | |
| 2006/0229613 A1 * | 10/2006 | Timm et al. | 606/61 |
| 2006/0265074 A1 | 11/2006 | Krishna et al. | |
| 2006/0271046 A1 * | 11/2006 | Kwak et al. | 606/61 |

* cited by examiner

*Primary Examiner*—Eduardo C Robert
*Assistant Examiner*—Christina Negrelli
(74) *Attorney, Agent, or Firm*—Nutter McClennen & Fish LLP

(57) ABSTRACT

Various methods and devices are provided for a facet replacement device. In one embodiment of the invention, a facet replacement device is provided and includes an elongate member matable to a first vertebra and a housing. The housing can have a connector formed thereon and matable to an adjacent second vertebra and an inner lumen formed therein. The housing can also include a deformable member disposed within the inner lumen and having an opening formed therein for slidably receiving at least a portion of the elongate member such that the elongate member can be angularly oriented relative to a longitudinal axis of the lumen.

22 Claims, 7 Drawing Sheets

FACET JOINT PROSTHESIS

BACKGROUND

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface which faces upward and an inferior articular surface which faces downward. Together the superior and inferior articular surfaces of adjacent vertebrae form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Subsequent surgery may also be required after a laminectomy, as a laminectomy predisposes the patient to instability and may lead to post-laminectomy kyphosis (abnormal forward curvature of the spine), pain, and neurological dysfunction. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

A number of devices are currently employed to correct such problems, such as artificial facet joints. None of these devices utilize geometries that allow for similar kinetics of a normal spine that would permit certain movements while resisting others.

Accordingly, there remains a need for improved systems and methods that are adapted to mimic the natural function of the facet joints.

SUMMARY

The present invention provides various methods and devices for replacing one or more facet joints in a patient's spine. In one embodiment, a facet replacement device is provided and includes an elongate member matable to a first vertebra, and a housing having a connector formed thereon and matable to an adjacent second vertebra. The housing can include a deformable member disposed within an inner lumen formed thereon, and the deformable member can have an opening formed therein for slidably receiving at least a portion of the elongate member such that the elongate member can be angularly oriented relative to a longitudinal axis of the lumen. In use, the elongate member can be adapted to slidably translate relative to the opening in the deformable member to allow flexion, extension, and lateral bending of adjacent vertebrae coupled thereto. The opening in the elongate member can be adapted to provide limited lateral motion, thereby providing resistance to anterior-posterior shear and axial rotation after the initial small motion.

While the deformable member can have a variety of configurations, in one embodiment it has a substantially cylindrical shape. The opening formed in the deformable member can extend along a central axis of the deformable member. The deformable member can also include a plurality of holes spaced around the opening and extending substantially parallel to the central axis of the deformable member. The device can also include a bearing disposed within the opening formed in the deformable member and adapted to facilitate slidable movement of the elongate member within the opening.

The housing can also have a variety of configurations, but in an exemplary embodiment the housing is substantially rigid and has a generally cylindrical shape that surrounds the deformable member. The connector can extend laterally from the cylindrical portion of the housing. In one embodiment, the connector can include a bore formed therethrough that is adapted to receive a portion of a bone anchor for anchoring the housing to a vertebra. In certain exemplary embodiments, the bore can have an oblong shape to allow a bone anchor to be positioned within the bore at a plurality of positions.

In another embodiment, a facet replacement system is provided and includes a first component adapted to couple to a first vertebra and having a deformable member disposed therein, and a second component adapted to couple to a second adjacent vertebra and having at least a portion that is receivable within the deformable member of the first component. The second component is adapted to slidably translate relative to a longitudinal axis of the first component to allow flexion, extension, and lateral bending of adjacent vertebrae coupled thereto. The second component can also be adapted to move laterally relative to the longitudinal axis of the first component to deform the deformable member and thereby provide resistance to anterior-posterior shear and axial rotation of adjacent vertebrae coupled thereto.

In one embodiment, the first component can include a first housing adapted to mate to a first lateral side of a first vertebra, and a second housing adapted to mate to a second lateral side of a first vertebra. The second component can include a first elongate member adapted to anchor to a first lateral side of a second vertebra, and a second elongate member adapted to anchor to a second lateral side of a second vertebra. At least a portion of the first elongate member can be positioned within a first deformable member disposed within the first housing, and at least a portion of the second elongate member can be positioned within a second deformable member disposed within the second housing. The system can also optionally include a cross-connector having a first end coupled to the first housing and a second end coupled to the second housing, and/or a cross-connector having a first end coupled to the first elongate member and a second end coupled to the second elongate member.

Methods for stabilizing adjacent vertebrae are also provided, and in one embodiment the method can include coupling a first component to a first vertebra and coupling a second component to a second adjacent vertebra and positioning at least a portion of the second component within a deformable member of the first component such that the second component translates along a longitudinal axis of the deformable member to allow flexion, extension, and lateral bending of the first and second vertebrae. The second component can also move laterally relative to the longitudinal axis of the deformable member to provide resistance to anterior-posterior shear and axial rotation of the first and second vertebrae.

In one embodiment, coupling the first component to the first vertebra can include implanting an anchor in the first vertebra and mating a connector formed on the first component to the anchor, and coupling the second component to the second vertebra can include implanting an anchor in the second vertebra and mating the second component to the anchor. In one exemplary embodiment, the anchor mated to the second component can be adapted to allow the second component to pivot relative to the second vertebra. In another exemplary embodiment, coupling the first component to a first vertebra can include anchoring a first housing to a first lateral side of the first vertebra and anchoring a second housing to a second lateral side of the first vertebra, and coupling the second component to a second vertebra can include anchoring a first elongate member to a first lateral side of the second vertebra and anchoring a second elongate member to a second lateral side of the second vertebra. At least a portion of the first elongate member can be positioned within a first deformable member disposed within the first housing, and at least a portion of the second elongate member can be positioned within a second deformable member disposed within the second housing. The method can also include coupling a first end of a cross-connector to the first housing and a second end of the cross-connector to the second housing, and coupling/or a first end of a cross-connector to the first elongate member and a second end of the cross-connector to the second elongate member.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for accommodating the natural function of the spine by allowing flexion, extension, and lateral bending of the spine, while providing resistance to anterior-posterior shear and axial rotation of the spine. A person skilled in the art will appreciate that, while the methods and devices are especially configured for use in restoring and/or replacing the facet joints and optionally other posterior elements of a patient's spine, the methods and devices can be used for a variety of other purposes in a variety of other surgical procedures.

Figure 1:
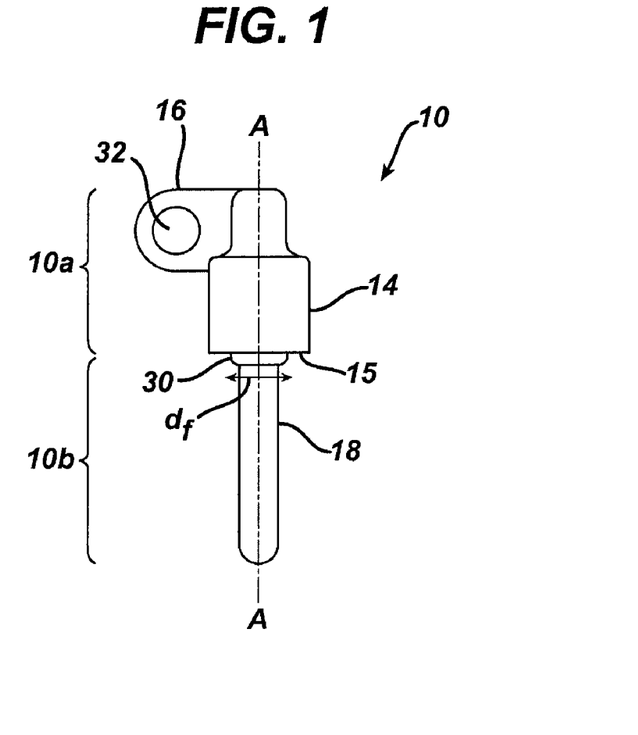
FIG. 1 is side view of one embodiment of a facet replacement device having a housing and an elongate member.
Figure 2:
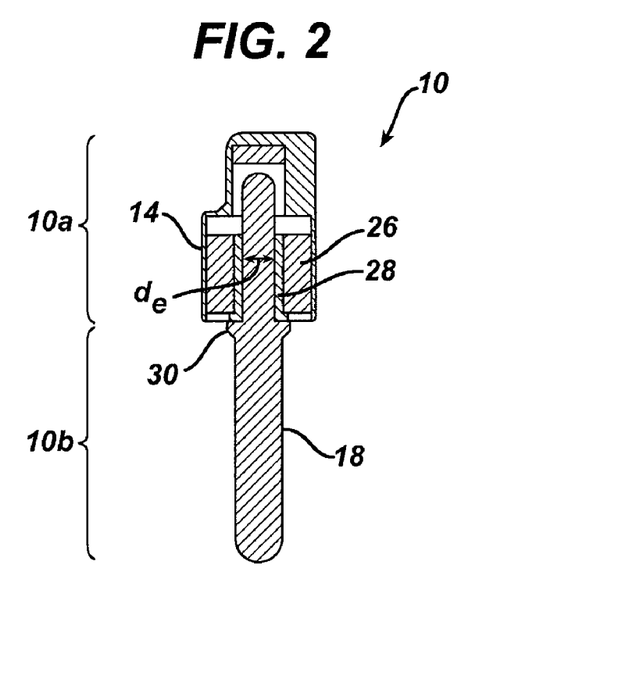
FIG. 2 is a cross-sectional view of the facet replacement device shown in FIG. 1.
Figure 3:
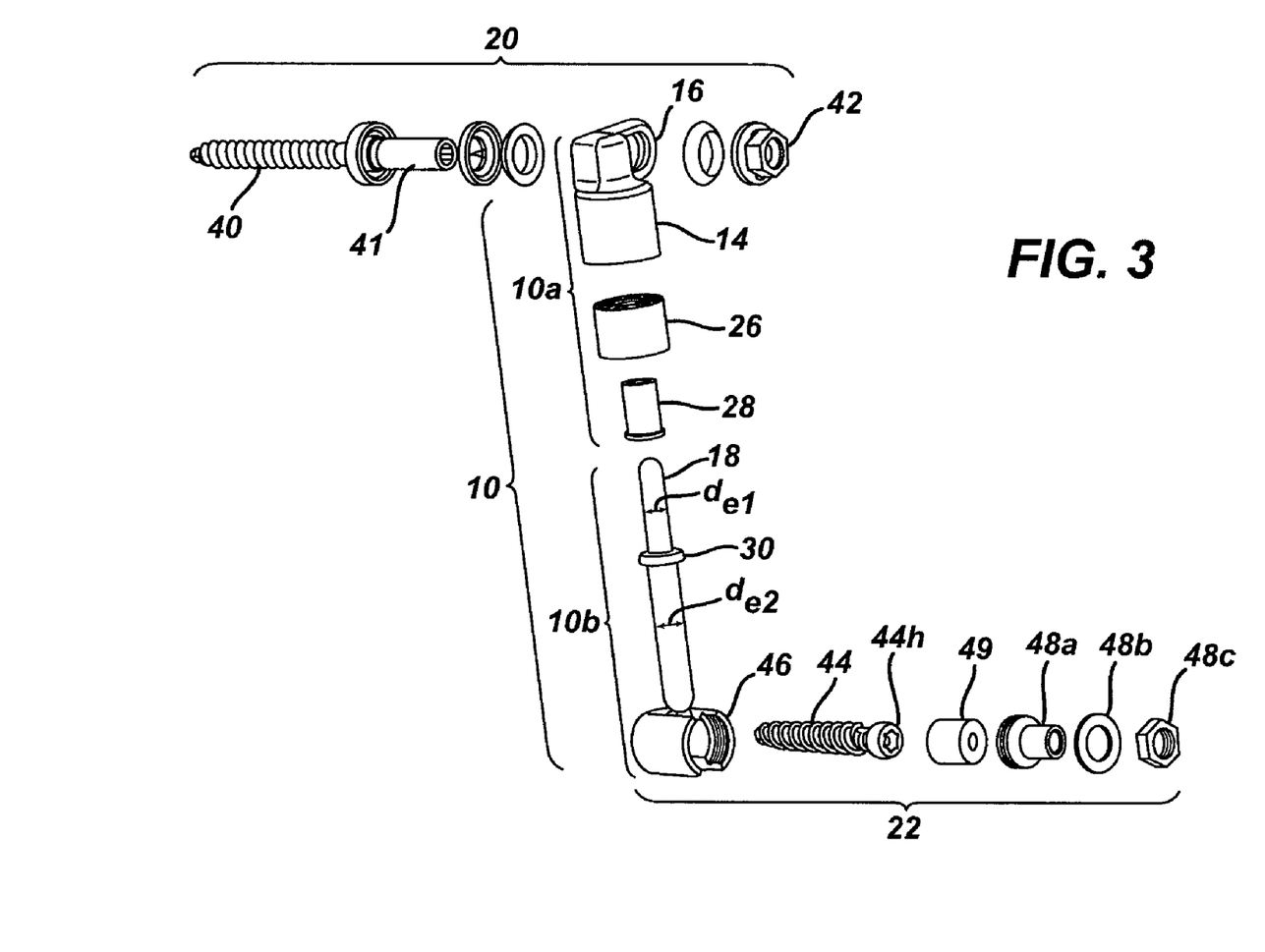
FIG. 3 is an exploded view of the facet replacement device shown in FIG. 1, showing anchors for coupling the housing and elongate member to adjacent vertebrae.

FIGS. 1-3 illustrate one exemplary embodiment of a facet replacement device 10. As shown, the device 10 generally includes a first member 10a that can be coupled to a first vertebra, e.g., a superior vertebra, and a second member 10b that can be coupled to a second adjacent vertebra, e.g., an inferior vertebra. While not shown, the first and second members 10a, 10b can be reversed such that the first member 10a can be coupled to the inferior vertebra and the second member 10b can be coupled to the superior vertebra. The first and second members 10a, 10b can also be movably coupled to one another. In particular, the first member 10a can include a housing 14 with a deformable member 26 disposed therein, and the second member 10b can include an elongate member 18 that is adapted to be received by the deformable member 26. In use, the deformable member 26 and the elongate member 18 cooperate to control movement of superior and inferior vertebrae relative to one another, and in particular they can allow flexion, extension, and lateral bending of the vertebrae preferably while providing resistance to anterior-posterior shear and axial rotation of the vertebrae.

The first member 10a of the device 10 can have a variety of configurations. In the illustrated exemplary embodiment, the first member 10a is in the form of a housing 14 that has a generally cylindrical configuration. As shown in FIG. 2, the housing 14 can include an inner lumen extending therethrough that is adapted to house the deformable member 26 therein. The housing 14 can also include a connector 16 (FIG. 1) extending laterally from a sidewall of the housing 14 and adapted to mate to a vertebra, e.g., the superior vertebra, as will be discussed in more detail below. The housing 14 and connector 16 can be formed from a variety of materials, but in an exemplary embodiment the housing 14 and the connector 16 are preferably substantially rigid to facilitate rigid mating to a vertebra.

The deformable member 26 housed in the inner lumen of the housing 14 can also have a variety of configurations, but it is preferably adapted to slidably receiving at least a portion of the elongate member 18 of the second member 10b to allow adjacent vertebrae mated to the first and second members 10a, 10b to flex and extend relative to one another. The deformable member 26 is also preferably adapted to allow limited lateral motion of the elongate member 18 relative to a longitudinal axis A of the first member 10a to provide resistance to anterior-posterior shear and axial rotation of the adjacent vertebrae coupled to the first and second members 10a, 10b.

Figure 4:
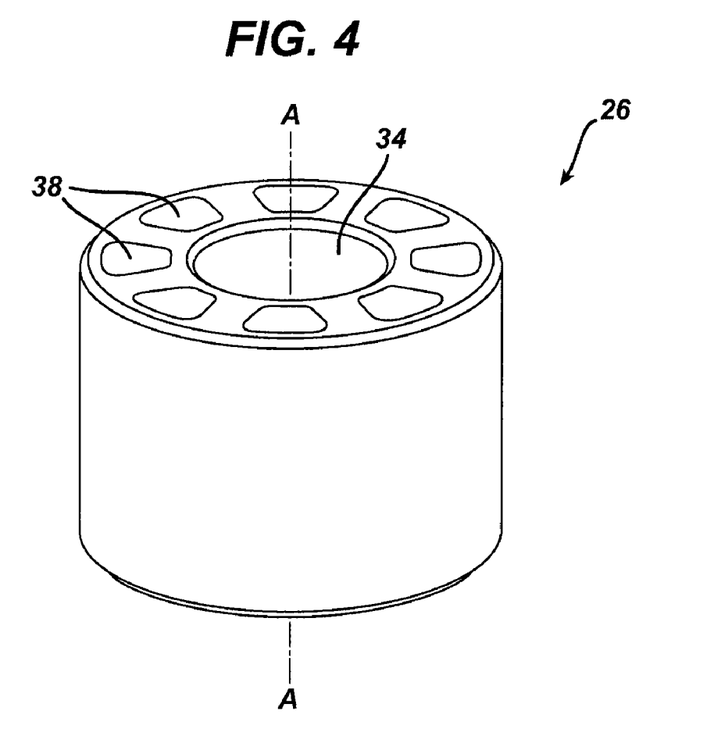
FIG. 4 is a perspective view of a deformable member of the facet replacement device shown in FIG. 1.
Figure 5:
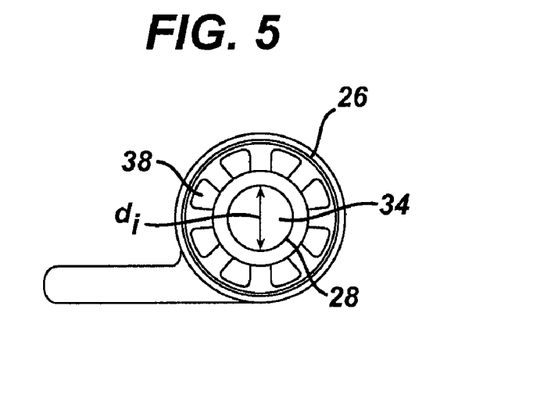
FIG. 5 is a top view of the deformable member of FIG. 4 disposed within the housing of FIG. 1.
Figure 6:
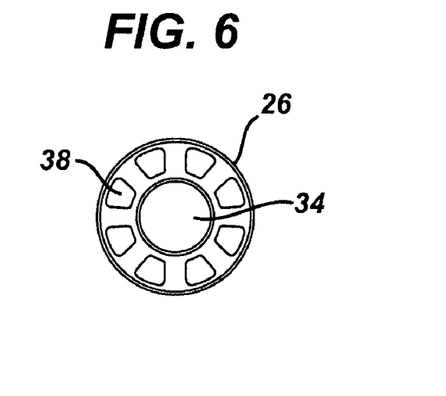
FIG. 6 is a top view of the deformable member shown in FIG. 4.

While the deformable member 26 can have a variety of configurations to allow flexion, extension, and lateral bending while providing resistance to lateral bending, anterior-posterior shear, and axial rotation, in the illustrated embodiment, shown in more detail in FIGS. 4-6, the deformable member 26 has a substantially cylindrical shape with an opening 34 formed therethrough. The opening 34 can be adapted to receive the elongate member 18 and it can extend along a central axis A of the deformable member 26, i.e., the central axis A of the device 10. The deformable member 26 can also include one or more holes 38 spaced around the opening 34 and extending substantially parallel to the central axis of the deformable member 26. The holes 38 are adapted to allow the deformable member 26 to bend, elongate, and otherwise compress during movement of the adjacent vertebrae coupled to the first and second members 10a, 10b. The deformable member can also be formed from a variety of materials. In certain exemplary embodiments, the deformable member is formed from an incompressible material, such that the deformable member is capable of deforming without changing volume. Where the material is incompressible, the use of holes or openings formed in the deformable member will allow the deformable member to deform during use. Exemplary materials for the deformable member 26 include, by way of non-limiting example, biocompatible polymers such as polyurethane, polyethylene, silicone, polyesters, polypropylene, polyethylene, or any combination of and metal such as above stainless steel, titanium, Nitinol, or cobalt chrome. A person skill in the art will appreciate that any number of holes 38 having any configuration can be formed in the deformable member 26 as long as they facilitate movement of the deformable member 26. Moreover, the deformable member 26 can have other configurations, such as a coil spring.

In use, the deformable member 26 is configured to replace the function of a facet joint. As indicated above, the deformable member 26 can provide axial translation, i.e., allowing sliding movement of the elongate member 18 within the opening 34 in the deformable member 26 along the axis A. During this movement, the deformable member 26 can rotate out of axis A and extend at an angle relative to the axis A. This causes portions of the deformable member 26 to deform, i.e., a portion of a wall of the deformable member 26 on the first lateral side will extend and a portion of a wall of the deformable member 26 on a second lateral side will compress. This allows flexion, extension, and lateral bending of the vertebrae with limited or no resistance from the deformable member 26. The only limit to the flexion and extension of the vertebrae can be a stop member, such as a flange 30 described in more detail below, which is adapted to limit penetration of the elongate member 18 through the deformable member 26. The deformable member 26 can also provide for anterior-posterior shear and axial rotation. During anterior-posterior shear and axial rotation, the deformable member 26 can translate out of the axis A while remaining substantially parallel to the axis A. For example, as the superior vertebrae moves in an anterior direction relative to the inferior vertebra, an anterior wall of the deformable member 26 will compress and a posterior wall of the deformable member 26 will extend, allowing for anterior-posterior shear of the adjacent vertebrae. Likewise, as the superior and inferior vertebrae axially rotate relative to one another, one wall of the deformable member 26 will compress as the opposite wall is extended.

The deformable member 26 can also include a bearing 28, shown in FIGS. 2 and 5, disposed within the opening 34 formed in the deformable member 26. The bearing 28 can have a variety of configurations, but in the illustrated embodiment it has a generally hollow cylindrically shape and is disposed around the inner surface of the opening 34 in the deformable member 26. The bearing 28 can be formed from a variety of materials, but in an exemplary embodiment it is formed from a material that resists wear as the elongate member 18 moves relative to the deformable member 26, as will be discussed in more detail below. By way of non-limiting example, the bearing 28 can be formed from a thin sheet of metal that coats the entire opening 34 extending through the deformable member 26. A person skilled in the art will appreciate that a number of techniques can be used to form a bearing 28 within the opening 34 in the deformable member 26, including a coating formed on a wall of the opening 34.

As noted above, the first member 10a can also include a connector 16 adapted to mate to a vertebra, e.g., the superior vertebra. While various techniques can be used to allow the connector 16 to mate to a vertebra, in the embodiment shown in FIGS. 1 and 3, the connector 16 is in the form of a tab extending laterally outward from the cylindrical portion of the housing and having a bore 32 extending therethrough for receiving a portion of a bone anchor. The connector 16 can be offset from the central axis A of the housing 14 so the connector 16 can be anchored to a vertebra at a location that is offset from the device 10. The bore 32 can vary in shape and size depending on the type of fastening element being used. For example, the bore 32 can have a circular shape, or it can have an oblong shape to allow a bone anchor to be positioned within the bore 32 at a plurality of positions relative to the connector 16. Various anchors can also be used to mate the connector 16 to bone. In an exemplary embodiment, as shown in FIG. 3, the bone anchor 20 is in the form of a bone screw having a threaded shank 40 and a head 41 adapted to extend through the bore 32 in the connector 16 and to mate with a fastening element 42, such as a locking nut, that is adapted to lock the connector 16 of the housing 14 to the head 41, and this to a vertebra.

The second member 10b of the facet replacement device 10 can also have a variety of configurations, but as indicate above and as shown in FIGS. 1-3, the second member 10b can be in the form of an elongate member 18 having a substantially cylindrical shape with first and second portions 18a, 18b. The first portion 18a of the elongate member 18 can be adapted to extend into and slidably move through the opening 34 formed in the deformable member 26, and the second portion 18b can be adapted to couple to a bone anchor for mating the second member 10b to a vertebra, e.g., the inferior vertebra. In an exemplary embodiment, the first portion 18a of the elongate member 18 has a substantially cylindrical shape with a diameter $d_{e1}$ that is only slightly less than an inner diameter $d_i$ (FIG. 5) of the opening 34 formed through the deformable member 26. Moreover, although not shown, the elongate member 18 does not need to be straight. The elongate member can be curved following an arc; and correspondingly, the opening in member 26 could follow the same arc to receive the curved elongate member.

As noted above, the second portion 18b of the elongate member 18 can be adapted to couple to a bone anchor to mate the second portion 18b to a vertebra. In one embodiment, the second portion 18b can have a diameter $d_{e2}$ that is different from the diameter $d_{e1}$ of the first portion 18a to provide secure mating of the second portion 18b to the bone anchor. The second portion 18b can have a variety of configurations depending on the type of bone anchor used, but in an exemplary embodiment the bone anchor 22 is in the form of a bone screw. As shown in FIG. 3, the bone screw is a polyaxial bone screw having a threaded shank 44 that is adapted to engage bone, and a U-shaped receiving head 46 that is configured to movably seat a head 44h formed on the threaded shank 44. The U-shaped receiving head 46 is also adapted to seat the second portion 18b of the elongate member 18 therein. As further shown in FIG. 3, the bone screw can include a locking element, such as a set screw 48a, which can mate to a nut 48b and washer 48c, for locking the second portion 18b of the elongate member 18 within the receiving head 46, thereby mating the second member to the inferior vertebra. The bone screw can also include an insert, such as a compression element 49, that is positioned between the second portion 18b of the elongate member 18 and the head 44h of the threaded shank 44. The compression element 49 is configured to allow the second portion 18b of elongate member 18 to be locked within the receiving head 46, while still allow free polyaxial movement of the threaded shank 44 relative to the receiving head 46. As a result, the elongate member 18 and the receiving head 46 fixedly mated thereto can together pivot and polyaxially move relative to the threaded shank 44 and vertebrae within which the shank 44 is implanted, thereby accommodating for the curvature of the spine as the elongate member 18 moves relative to the deformable member 26. A person skilled in the art will appreciate that a variety of types of bone screws can be used, including monoaxial screws. The particular type of bone anchor used may depend on the type of disc implant used, and in particular on the degrees of freedom provided by the disc implant.

Figure 7:
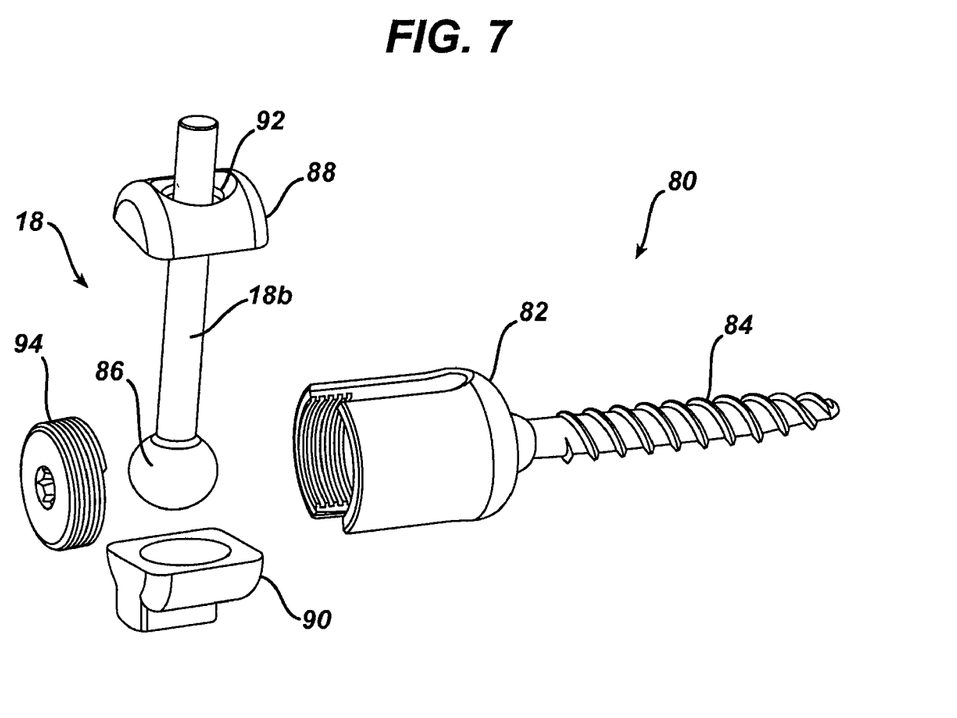
FIG. 7 is a perspective view of an embodiment of a bone anchor for movably coupling an elongate member of a facet replacement device to a vertebra.

FIG. 7 illustrates another embodiment of a bone anchor for movably coupling the elongate member to a vertebra. In this embodiment, the bone anchor 80 is in the form of a monoaxial screw having a receiving head 82 with a threaded shank 84 formed thereon and extending distally therefrom. The second portion 18b of the elongate member 18 includes a spherical member or ball 86 formed on a terminal end thereof that is adapted to be disposed within a socket formed in the receiving head 82. In particular, the receiving head 82 can include first and second inserts 88, 90 that are receivable therein. One of the inserts, i.e., insert 88, can include a bore 92 extending therethrough for receiving the second portion 18b of the elongate member 18, and each insert 88, 90 can also include a concave recess formed therein. When the inserts 88, 90 are disposed within the receiving head 82, the ball 86 on the second portion 18b of the elongate member 18 will be movably capture within the recesses to allow polyaxial movement of the elongate member 18 relative to the bone anchor 80. As further shown, a locking mechanism, such as a set screw 94, can be used to lock the inserts 88, 90 and the ball 86 within the receiving head 82.

The second member 10b can also include other features, such as a stop member formed on a portion of the elongate member to limit movement thereof relative to the deformable member. While the stop member can have a variety of shapes and sizes, in the illustrated exemplary embodiment the stop member is in the form of a substantially circular flange 30 disposed around the elongate member 18 between the first and second portions 18a, 18b. The flange 30 can be adapted to abut against an end wall 15 of the housing 14 adjacent to the opening to limit penetration of the elongate member 18 through the deformable member 26. Accordingly, the flange 30 preferably has an extent, e.g., a diameter $d_f$ (FIG. 1), that is larger than the diameter $d_i$ (FIG. 5) of the opening 34 in the deformable member 26. In another exemplary embodiment, a terminal end of the elongate member 18 can also include a flange (not shown) formed thereon to prevent removal of the elongate member 18 from the deformable member 26.

Figure 8:
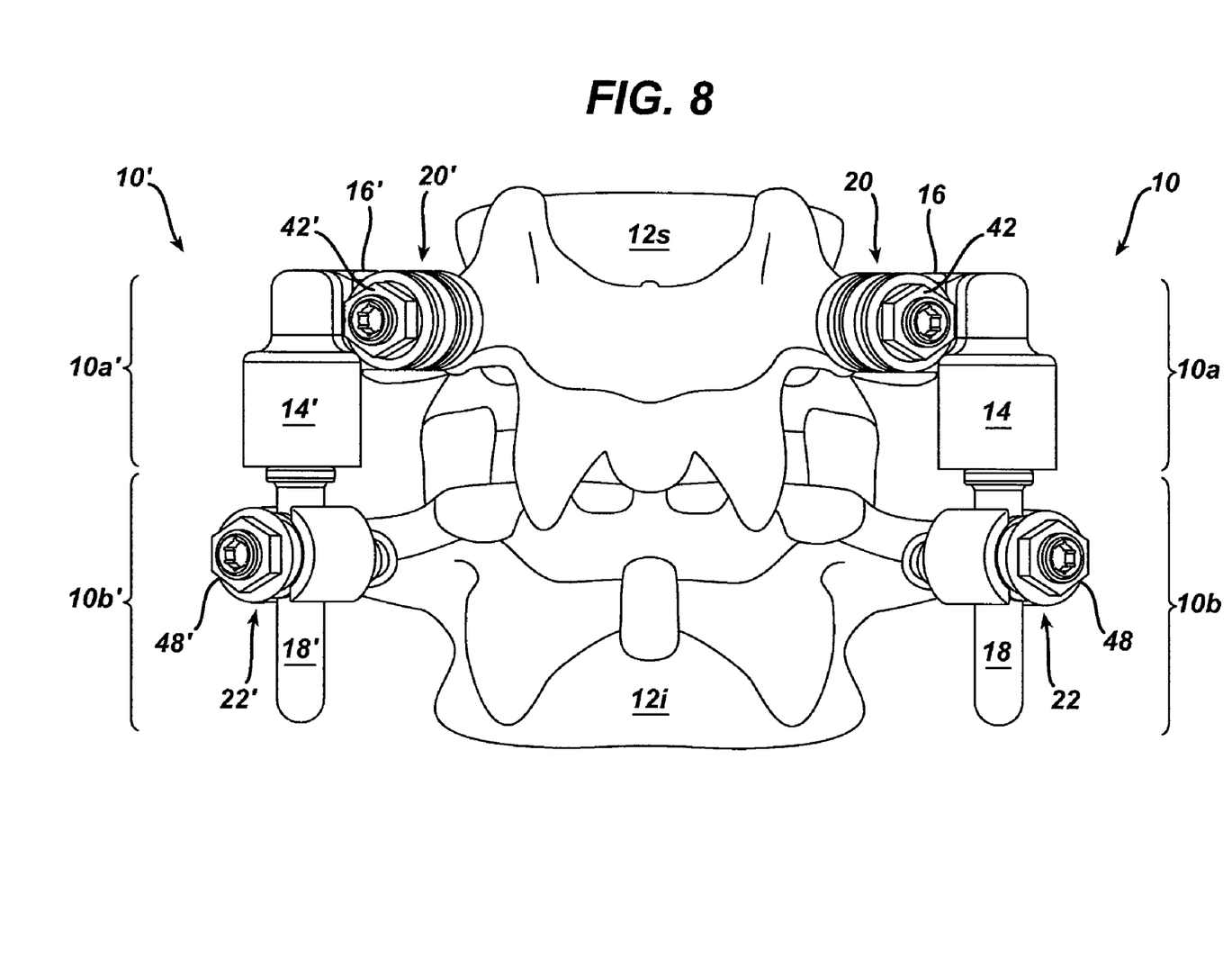
FIG. 8 is a front view of two facet replacement devices shown in FIG. 1 coupled to adjacent vertebrae.

In use, one or more facet replacement devices can be coupled to one or more adjacent vertebrae. By way of non-limiting example, FIG. 8 illustrates first and second facet replacement devices 10, 10' coupled to adjacent superior and inferior vertebrae 12s, 12i. In particular, the first facet replacement device 10 is coupled to a first lateral side of the superior and inferior vertebrae 12s, 12i, and the second facet replacement device 10' is coupled to a second lateral side of the superior and inferior vertebrae 12s, 12i. While only two devices are shown, additional devices can be coupled to additional vertebrae located along the patient's spinal column. An artificial disc implanted can also optionally be implanted between the adjacent vertebrae 12s, 12i in conjunction with the facet replacement device 10. A person skilled in the art will appreciate that the facet replacement devices disclosed herein can be used with a natural disc or with an artificial disc. In an exemplary embodiment, where an artificial disc is used, the disc is preferably one which allows movement of the adjacent vertebrae relative to one another. In one embodiment, an artificial disc having a ball and socket joint is used which provides one degree of freedom in the sagittal plane. By way of non-limiting example, one exemplary artificial disc for use with the present invention is described in U.S. patent application Ser. No. 11/351,710, filed on Feb. 10, 2006, and entitled "Intervertebral Disc Prosthesis Having Multiple Bearing Surfaces." In another embodiment, the artificial disc can provide two or more degrees of freedom, such as the Charité™ artificial disc manufactured by DePuy Spine, Inc.

Figure 9:
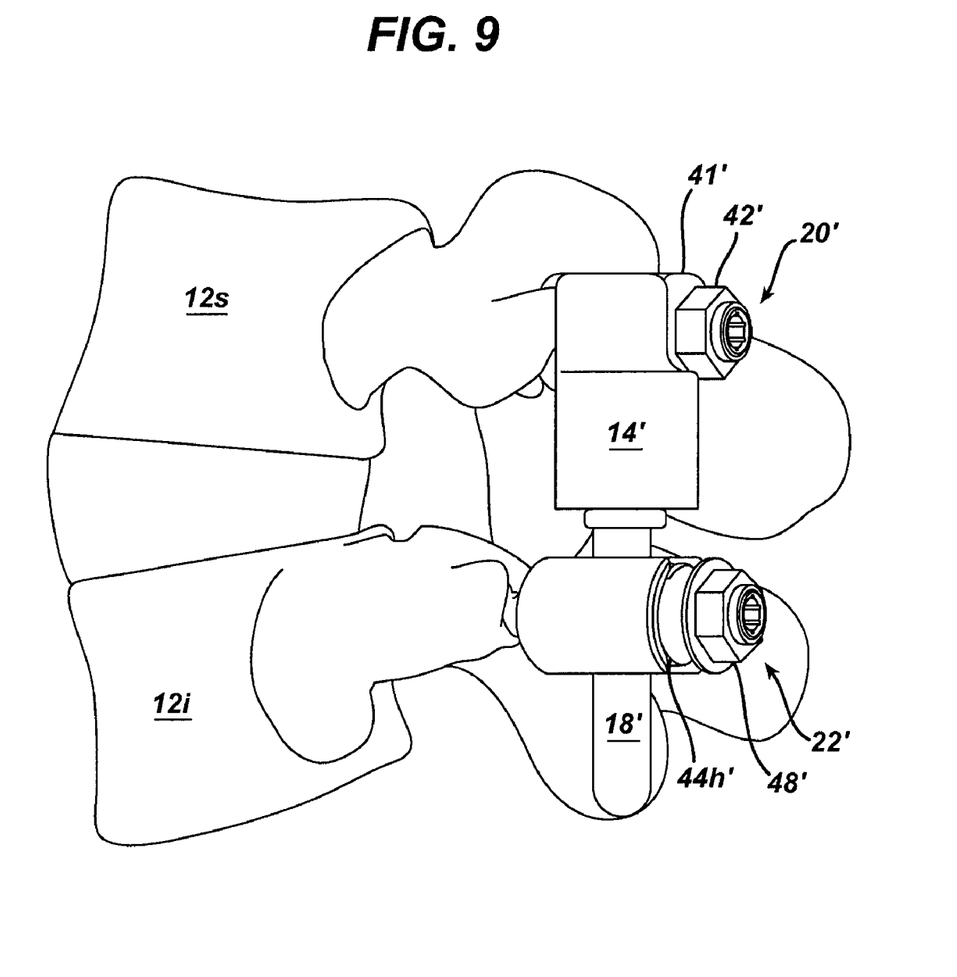
FIG. 9 is a side perspective view of one of the facet replacement devices and the adjacent vertebrae of FIG. 8.

As shown in FIGS. 8-9, two bone screws 20, 20' are implanted in opposed lateral sides of a superior vertebra 12s, and two bone screws 22, 22' are implanted on opposed lateral sides of an inferior vertebra 12i. Once the bone screws 20, 20', 22, 22' are implanted, the first member 10a, 10a' of each facet replacement device 10, 10' can be coupled to the bone screw 20, 20' implanted in the superior vertebra by positioning the connector 16, 16' such that the head 41, 41' of each bone screw 20, 20' extends through the connector 16, 16' in the housing 14, 14'. The fastening element 42, 42' can then be loosely threaded onto the head 41, 41' of each bone screw 22, 22' to loosely attach the housings 14, 14' to the bone screws 22, 22'. The housings 14, 14' can then be angularly adjusted as desired. The elongate members 18, 18' of the devices 10, 10' can be coupled to bone screws 22, 22' in the inferior vertebra 12i by inserting the elongate members 18, 18' through the opening in the deformable members (not shown) of the housings 14, 14' and positioning the second portion 10b, 10b' of the elongate members 18, 18' within the receiving heads 44h, 44h' of the bone screws 22, 22'. The fastening elements 48, 48' can be inserted into the receiving heads 44h, 44h' to loosely mate the elongate members 18, 18' to the inferior vertebra 12i. Once the housings 14, 14' and the elongate members 18, 18' are properly positioned, the fastening elements 42, 42', 48, 48' can be tightened to maintain the housings 14, 14' and the elongate members 18, 18' in a fixed position relative to the superior and inferior vertebra 12s, 12i. A person skilled in the art will appreciate that the bone screws, the housings, and the elongate members can be implanted and adjusted in any order. In one exemplary embodiment, the elongate member is positioned as desired and the housing is then positioned as necessary based on the positioning of the elongate member. Once implanted, the deformable member 26 can allow flexion, extension, lateral bending, anterior-posterior shear, and axial rotation, as previously explained, in such a way that substantially accommodates the natural function of the facet joints thereby restoring movement to the adjacent vertebrae.

Figure 10:
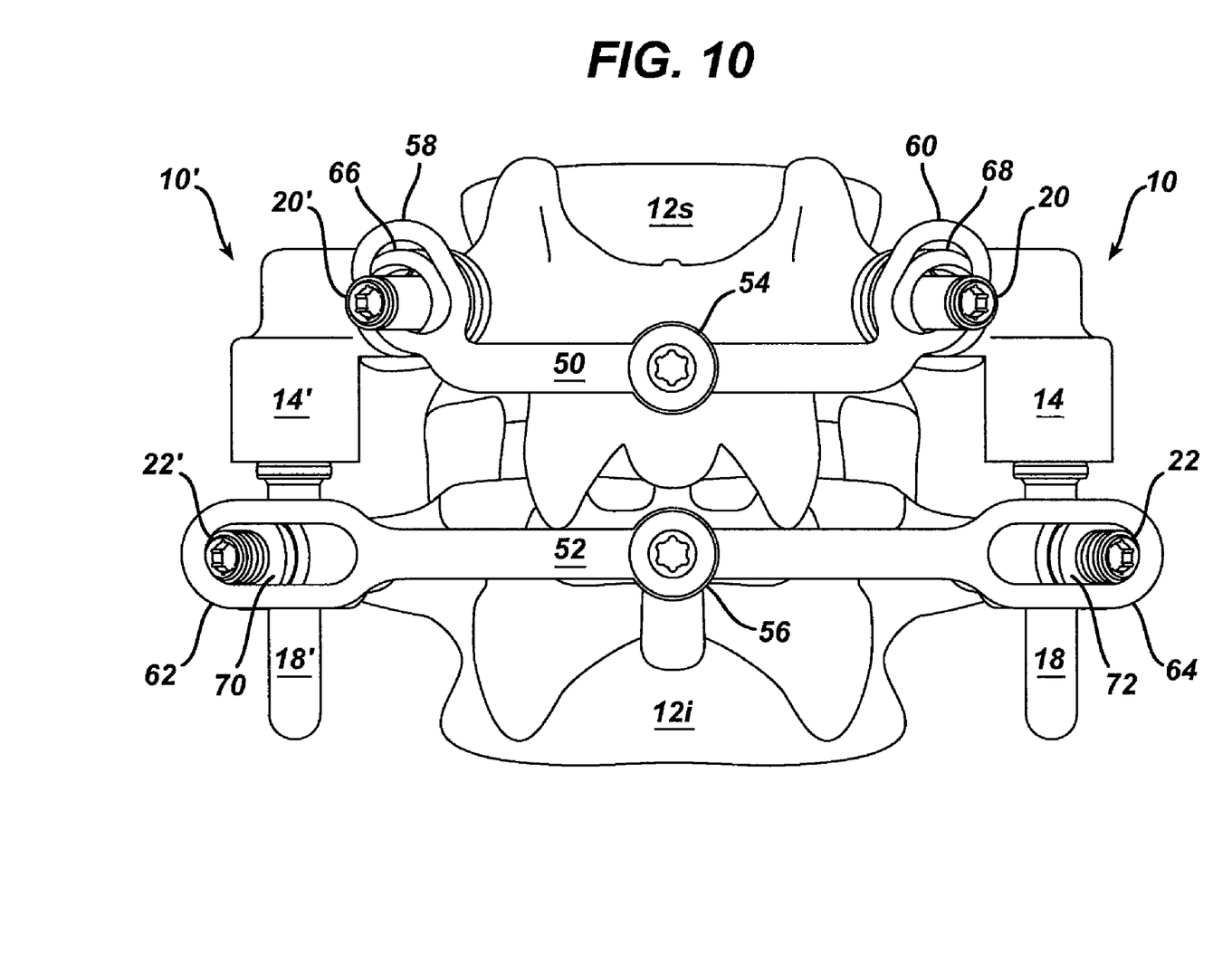
FIG. 10 is a front view of the facet replacement devices and adjacent vertebrae of FIG. 8, showing first and second cross connectors mated thereto.

Additional devices may be provided with the system described above to provide further structure to the system. In one embodiment, one or more cross-connectors can be positioned across the superior and inferior vertebrae 12s, 12i and attached to the facet replacement devices to minimize the potential for loosening of the bone anchors that mate the facet replacement devices to bone. FIG. 10 illustrates a first cross-connector 50 having opposed first and second ends 58, 60 that are coupled to the bone anchors 20, 20' implanted in the superior vertebra, and a second cross-connector 52 having opposed first and second ends 62, 64 that are coupled to the bone anchors 22, 22' in the inferior vertebra. Each cross-connector 50, 52 can have a variety of configurations, but in the illustrated embodiment each cross-connector 50, 52 has a generally elongate, plate-like configuration. The terminal end of each cross-connector 50, 52 can include an opening 66, 68, 70, 72 extending therethrough for receiving the anchors 20, 20', 22, 22' that mate the first and second facet replacement devices 10, 10' to bone. The openings 66, 68, 70, 72 can have any shape, but in the illustrated embodiment each opening 66, 68, 70, 72 has an oblong shape to facilitate positioning of the cross-connectors 50, 52 relative to the bone anchors 20, 20', 22, 22'. Each cross-connector 50, 52 can also include an attachment element 54, 56, such as a pin or a bone screw, to facilitate coupling to the superior and inferior vertebrae 12s, 12i. While the attachment elements 54, 56 can be positioned in a variety of locations on the cross-connectors 50, 52, in the illustrated embodiment the attachment elements 54, 56 are located at a substantial midpoint of each cross-connector 50, 52. As further shown in FIG. 10, the first cross-connector 50 can have angled terminal ends 58, 60, while the second cross-connector 52 can have terminal ends 62, 64 that are substantially straight. In one embodiment, the terminal ends 58, 60 of the first cross-connector 50 are angled upward to allow the first cross-connector 50 to span laterally across the vertebra and below the spinous process while having the terminal ends 58, 60 anchored to the pedicles of the vertebra. A person skilled in the art will appreciate that the cross-connectors 50, 52 can have a variety of other configurations and can both be angled, straight, or have any other configuration that would allow the cross-connectors 50, 52 to span across the vertebrae and couple to the facet replacement devices 10, 10' implanted in opposed lateral sides of adjacent vertebrae 12s, 12i. In use, the first and second cross-connectors 50, 52 can be adapted to provide rotational support and to reduce the potential for loosening of the bone screws implanted in the superior and inferior vertebrae 12s, 12i. A person skilled in the art will appreciate that any number of cross-connectors can be used with the facet replacement system.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A facet replacement device, comprising:
   an elongate member matable to a first vertebra;
   a housing matable to an adjacent second vertebra and having a blind bore formed therein, and a deformable member disposed within the a blind bore and having an opening formed therein for slidably receiving at least a portion of the elongate member such that the elongate member can be angularly oriented relative to a longitudinal axis of the inner lumen; and
   a bearing disposed within the opening formed in the deformable member, and adapted to facilitate slidable movement of the elongate member within the opening;
   wherein the elongate member and the opening formed in the deformable member are curved.

2. The device of claim 1, wherein the elongate member is adapted to slidably translate relative to the opening in the deformable member.

3. The device of claim 1, wherein the elongate member is adapted to provide limited lateral motion relative to the housing.

4. The device of claim 1, wherein the deformable member has a substantially cylindrical shape.

5. The device of claim 4, wherein the opening formed in the deformable member extends along a central axis of the deformable member.

6. The device of claim 5, wherein the deformable member includes a plurality of holes.

7. The device of claim 6, wherein the plurality of holes are spaced around the opening and extend substantially parallel to the central axis of the deformable member.

8. The device of claim 1, wherein at least a portion of the housing surrounding the deformable member is rigid.

9. The device of claim 1, wherein the housing includes a generally cylindrical portion that houses the deformable member, and a connector extending from the cylindrical portion of the housing.

10. The device of claim 9, wherein the connector includes a bore formed therethrough that is adapted to receive a portion of a bone anchor for anchoring the housing to a vertebra.

11. The device of claim 1, wherein the elongate member and the opening formed in the deformable member are linear.

12. A facet replacement system, comprising:
   a first component adapted to couple to a first vertebra and having a deformable member disposed therein; and
   a second component adapted to couple to a second adjacent vertebra and having at least a portion that is receivable within the deformable member of the first component, the second component being adapted to slidably translate relative to a longitudinal axis of the first component to allow flexion and extension of adjacent vertebrae coupled thereto, and being configured to move laterally to compress and elastically deform the deformable member;
   wherein the second component is adapted to provide limited lateral motion relative to the longitudinal axis of the first component to provide resistance to anterior-posterior shear and axial rotation of adjacent vertebrae coupled thereto; and
   wherein the deformable member includes an opening formed therethrough and extending along a central axis of the deformable member, and the deformable member includes a plurality of holes.

13. The system of claim 12, wherein the plurality of holes are spaced around the opening and extend substantially parallel to the central axis of the deformable member.

14. The system of claim 12, further comprising a bearing disposed within the opening formed in the deformable member and adapted to facilitate slidable movement of the second component within the opening.

15. The system of claim 12, wherein the first component includes a housing that houses the deformable member and a connector formed thereon that extends from the housing, the connector including a bore formed therethrough that is adapted to receive a portion of a bone anchor for anchoring the housing to a first vertebra.

16. The system of claim 15, wherein the bore is oblong to allow a bone anchor to be positioned within the bore at a plurality of positions.

17. A facet replacement system, comprising:
   a first component adapted to couple to a first vertebra and having a deformable member disposed therein; and
   a second component adapted to couple to a second adjacent vertebra and having at least a portion that is receivable within the deformable member of the first component, the second component being adapted to slidably translate relative to a longitudinal axis of the first component to allow flexion and extension of adjacent vertebrae coupled thereto, and being configured to move laterally to compress and elastically deform the deformable member;
   wherein the second component is adapted to provide limited lateral motion relative to the longitudinal axis of the first component to provide resistance to anterior-posterior shear and axial rotation of adjacent vertebrae coupled thereto;
   wherein the first component comprises a first housing adapted to mate to a first lateral side of a first vertebra, and a second housing adapted to mate to a second lateral side of a first vertebra, and the second component comprises a first elongate member adapted to anchor to a first lateral side of a second vertebra, and a second elongate member adapted to anchor to a second lateral side of a second vertebra, at least a portion of the first elongate member being positioned within a first deformable member disposed within the first housing, and at least a portion of the second elongate member being positioned within a second deformable member disposed within the second housing.

18. The system of claim 17, further comprising a cross-connector having a first end coupled to the first housing and a second end coupled to the second housing.

19. The system of claim 17, further comprising a cross-connector having a first end coupled to the first elongate member and a second end coupled to the second elongate member.

20. A method for stabilizing adjacent vertebrae, comprising:
coupling a first component to a first vertebra;
coupling a second component to a second adjacent vertebra and positioning at least a portion of the second component within a deformable member of the first component such that the second component translates along a longitudinal axis of the deformable member and moves laterally to compress the deformable member;
wherein during anterior-posterior shear and axial rotation of the first and second vertebrae, the second component moves laterally by a limited amount relative to the longitudinal axis of the deformable member to provide resistance to anterior-posterior shear and axial rotation;
wherein coupling the first component to a first vertebra comprises anchoring a first housing to a first lateral side of the first vertebra, and anchoring a second housing to a second lateral side of the first vertebra, and wherein coupling the second component to a second vertebra comprises anchoring a first elongate member to a first lateral side of the second vertebra, and anchoring a second elongate member to a second lateral side of the second vertebra, at least a portion of the first elongate member being positioned within a first deformable member disposed within the first housing, and at least a portion of the second elongate member being positioned within a second deformable member disposed within the second housing.

21. The method of claim 20, further comprising coupling a first end of a cross-connector to the first housing and a second end of the cross-connector to the second housing.

22. The method of claim 20, further comprising coupling a first end of a cross-connector to the first elongate member and a second end of the cross-connector to the second elongate member.

* * * * *